United States Patent
Valdes et al.

(10) Patent No.: US 6,224,378 B1
(45) Date of Patent: May 1, 2001

(54) METHOD AND APPARATUS FOR DENTAL TREATMENT USING HIGH PRESSURE LIQUID JET

(75) Inventors: Juan C. Valdes, Alta Loma; Randal Bailey, Lake Forest; Steve Baldwin, Berkeley; Rex E. Doherty, Orinda, all of CA (US)

(73) Assignee: SurgiJet, Inc., Irvine, CA (US)

( * ) Notice: Subject to any disclaimer, the term of this patent is extended or adjusted under 35 U.S.C. 154(b) by 0 days.

(21) Appl. No.: 08/890,496

(22) Filed: Jul. 9, 1997

(51) Int. Cl.$^7$ ........................................... A61C 5/02
(52) U.S. Cl. ........................ 433/224; 433/81; 433/88
(58) Field of Search .................. 433/80, 81, 88, 433/215, 216, 82, 84, 86; 601/161, 162, 165

(56) References Cited

U.S. PATENT DOCUMENTS

| | | | |
|---|---|---|---|
| 3,590,813 | * | 7/1971 | Roszyk ........................... 601/162 |
| 3,624,907 | * | 12/1971 | Brass et al. ...................... 433/81 |
| 3,930,505 | * | 1/1976 | Wallach . |
| 3,962,790 | * | 6/1976 | Riitano et al. .................... 433/81 |
| 4,021,921 | * | 5/1977 | Detaille ............................ 433/81 |
| 4,060,600 | * | 11/1977 | Vit .................................. 433/216 |
| 4,215,476 | * | 8/1980 | Armstrong ........................ 433/80 |
| 4,247,288 | * | 1/1981 | Yoshii et al. ...................... 433/81 |
| 4,608,017 | * | 8/1986 | Sadohara .......................... 433/81 |
| 4,872,837 | * | 10/1989 | Issalene et al. .................... 433/80 |
| 4,957,436 | * | 9/1990 | Ryder ............................... 433/88 |
| 5,029,576 | * | 7/1991 | Evans, Sr. ....................... 601/162 |
| 5,601,430 | * | 2/1997 | Kutsch et al. ................... 433/215 |
| 5,620,414 | * | 4/1997 | Campbell .......................... 604/22 |

* cited by examiner

Primary Examiner—Cary E. O'Connor
(74) Attorney, Agent, or Firm—Harris Zimmerman (57) ABSTRACT

A method and apparatus for dental procedures using a dental hydrojet tool having a cannula extending therefrom. The cannula is connected to a source of high pressure liquid, and delivers a high velocity, high pressure jet. For root canal procedures, the cannula is directed through an opening formed in the crown of the tooth, and the hydrojet is directed at the pulp, nerve and vascular tissue within the interior chamber. The jet may comprise medical-grade saline, disinfectant, antibiotic or abrasive solutions. All the soft tissue within the tooth is cut, excised, emulsified, and aspirated out of the tooth. The time required to excise, emulsify, and aspirate all the soft tissue within a typical molar is on the order of 10–240 seconds. The interior chamber of the tooth is completely aspirated and verified visually for completion of removal of all soft tissue, and then packed with an appropriate filler material, and the opening in the top of the tooth is filled or provided with a prosthetic crown. The fluid jet may comprise a pulsed jet formed by a pulse intensifier device in the handpiece of the dental hydrojet tool, or a steady stream jet emanating from the orifice. The jet may be used for caries removal, plaque and calculus removal, and soft tissue surgery.

30 Claims, 8 Drawing Sheets

METHOD AND APPARATUS FOR DENTAL TREATMENT USING HIGH PRESSURE LIQUID JET

BACKGROUND OF THE INVENTION

The present invention relates to instruments for carrying out dental procedures, and more specifically to carrying out such procedures using a high pressure liquid jet.

It is known in the prior art and in common dental practice to carry out most treatments using mechanical techniques. For example, in endodontics, which often involves many root canal procedures, a diseased tooth is first diagnosed, and then an opening is drilled through the crown of the tooth into the pulp chamber thereof. After the tooth is isolated and the field sterilized, the pulp, consisting primarily of blood-rich tissue and nerve fiber and necrotic components, is then aspirated. There remains within the pulp chamber the primary nerve fibers and blood vessels that sustain the tooth. These tissues extend from extremely fine openings in the apex of the root(s) of the tooth through a narrow channel(s), and cannot be removed solely by aspiration.

Typically, a file is then inserted into the narrow channel(s) to displace and abrade the nerve and blood vessel tissue. Increasingly larger files are inserted, whereby the narrow channel(s) is cleared of all soft tissue. After cleaning and preparation, the pulp chamber and root channel(s) are filled with a sterile solid material, and the drilled opening is filled with standard gold, silver, or other dental filling preparations.

This typical procedure is labor-intensive, resulting in a high cost factor for the dentist's time as well as skill and experience. Moreover, the procedure may be painful, and sufficient local anesthetic must be injected to completely numb the area of the tooth for the relatively long time that the procedure requires.

Complications known to result from a root canal procedure may include infection arising from incomplete removal of the diseased tissue within the canal and pulp chamber, or the introduction of other infectious bacteria into those spaces during the procedure. In addition, the dentist may inadvertently perforate the tooth; e.g., by driving a file instrument through the apical opening at the base of the root, and the opening thus formed may provide a vector for renewed infection and inflammation. Not infrequently, drug therapy including a strong antibiotic is prescribed after the procedure to forestall these complications. Other complications include broken instruments lodged in the tooth, or fracture of the root or body of the tooth.

Recent innovations in this dental procedure include the use of laser light delivered into the pulp chamber and root channel by an optical fiber. The high power optical energy vaporizes the pulp and nerve tissue, and is inherently sterilizing. However, the products of tissue combustion may contaminate the interior of the chamber and root channel, and the laser pulses may not contact all of the tissue in the narrow root channel, causing very unsatisfactory results. To avoid these results, there is a tendency to apply an excess of laser energy, which may overheat the tooth and surrounding tissue and cause necrosis. In addition, laser energy impacting on pre-existing metallic fillings may cause dangerous reflected beams and unforeseen damage.

As another example, in periodontal practice, which typically includes gingivectomy procedures, the gingiva are usually resected using a scalpel, and scaling and root planing are accomplished with specialized steel tools. These procedures and most other dental procedures are executed with mechanical drills, burrs, and cutting wheels.

Innovations such as ultrasound-driven scaling instruments, high power lasers for caries removal, and the like have not substantially altered the reliance of the dental profession on the same mechanical tools that have been in use for almost a century. All such mechanical tools generate high levels of vibration and sound that are directly conducted through bone to the ears of the patient, resulting in patient comfort problems. Also, the mechanical tools, as well as ultrasound tools, generate substantial amounts of heat in very localized areas, causing direct pain stimulation. Water spray devices are provided to remove this heat, but may not be effective at the point source of the heat. In this regard, the heat generated by dental lasers may pose the greatest problem.

Clearly the prior art shows an unmet need for improved dental instruments that can carry out a wide range of dental treatment procedures without generating heat, noise, and vibration as they operate on the patient's teeth.

SUMMARY OF THE PRESENT INVENTION

The present invention generally comprises an apparatus and methods for dental treatments that overcome the problems associated with current mechanical and dental techniques and instruments. In one aspect, the invention comprises a technique for removing the soft tissue from within a human or animal tooth, whereby infectious, inflamed and necrotic tissue may be removed and the tooth and periodontal structures restored to a healthy condition. A salient aspect of the invention is that the invention obviates the need for files and other mechanically abrasive displacement tools, employing instead a high pressure jet of water or other liquid directed at the soft tissue within the tooth to excise, emulsify and aspirate the soft tissue. The soft tissue may comprise the pulp, nerve tissue and blood vessels that extend from the surrounding jaw bone through the apex of each tooth root into the root channel and to the pulp chamber of the tooth.

The invention provides a dental hydrojet tool having a handpiece and a cannula extending therefrom. The cannula is connected to a source of high pressure water or other liquid, and includes a distal orifice to deliver a high velocity, high pressure jet. The pressure range of the high pressure source is approximately 500–60,000 psi, and the jet orifice is approximately 10–800 microns in diameter. The cannula may also provide aspiration to remove the fluid from the jet as well as tissue, or aspiration may be provided by a second cannula connected to a vacuum aspiration unit. An exemplary device is described in U.S. Pat. No. 5,562,692, commonly assigned herewith.

To initiate the method of the invention, a tooth that is diagnosed as diseased and in need of a pulpectomy/root canal procedure is opened; that is, a hole is made in the crown of the tooth using a standard dental grinding or drilling instrument. The tooth is then isolated using a dental dam or similar protective shield.

The cannula of the hydrojet tool is then directed through the newly formed hole in the crown of the tooth, and a jet of liquid is directed at the pulp and nerve and vascular tissue within the interior chamber of the tooth. The fluid may comprise medical-grade saline solution, and/or a disinfectant solution and/or an antibiotic solution and/or an abrasive solution. In the pressure range and jet diameter formed by the hydrojet tool, all the soft tissue within the tooth is cut, excised, emulsified, and aspirated out of the tooth. Aspiration may be provided by the hydrojet tool, or by the cannula of a standard dental aspiration device.

A salient aspect of the method of the invention is that the hydrojet easily removes all the soft tissue within the tooth, but is limited in its ability to cut or erode the hard calcified tooth tissue. Likewise, the jet lacks the velocity to cut through the apical root openings through which the nerve fibers and blood vessels enter the root channels from the surrounding jaw tissue. As a result, this process of pulpectomy/root canal progresses to a self-limiting extent and for example, cannot pierce the apical openings if they are naturally closed, whereby a source or complications known to result from prior art procedures. In addition, the use of antiseptic or antibiotic solutions reduce the possibility of post-procedure infection if the apical openings where to be damaged.

Moreover, the time required to excise, emulsify, and aspirate all the soft tissue within a typical molar is on the order of 10–240 seconds, so that far less time and labor is expended in the procedure. This reduction in time to complete the removal step reduces the need for local anesthesia, reduces the time that the patient may experience pain (if any), and overall increases throughput in a dental practice.

The interior chamber of the tooth is then completely aspirated and verified for completion of removal of all soft tissue. The interior chamber is then packed with an appropriate filler material known in the prior art, and the opening in the top of the tooth is filled or provided with a prosthetic crown, as is known in the dental art.

It should be noted that the fluid jet may comprise a pulsed jet formed by a pulse intensifier device in the handpiece of the dental hydrojet tool, as described in the US patent to Bair referenced above. Alternatively, the handpiece may be connected to a source of high pressure fluid to form a steady stream jet emanating from the orifice. The handpiece may be directed at other surfaces and structures to carry out endodontal, periodontic, surgical, and restorative procedures such as gingivectomy, removal of granulation tissue, mucoosseous surgery, caries removal, scaling and removal of plaque and calculus, and extractions and tissue incisions.

BRIEF DESCRIPTION OF THE DRAWING

FIG. 16a is an enlarged end view of a further embodiment of the output tip of the dental instrument depicted in FIG. 14.

FIG. 16b is a fragmentary cross-sectional view of the output tip, taken along line 16b–16b of FIG. 16a.

DESCRIPTION OF THE PREFERRED EMBODIMENT

The present invention generally comprises an apparatus and methods for dental treatments that overcome the problems associated with current mechanical and dental techniques and instruments. In one aspect, the invention comprises a technique for carrying out a pulpectomy or root canal: that is, removing the soft tissue within the tooth by excising, emulsifying and aspirating the soft tissue.

Figure 1:
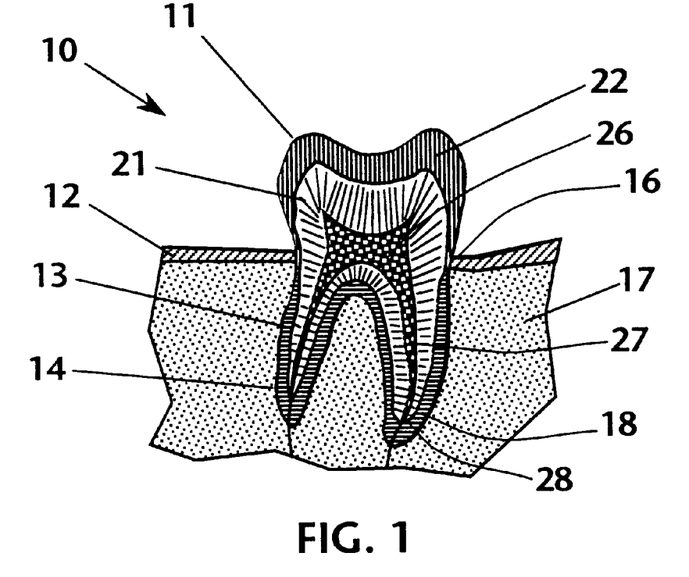
FIG. 1 is a cross-sectional elevation of a typical human tooth prior to undergoing the pulpectomy/root canal procedure of the present invention.

With regard to FIG. 1, a typical human tooth 10 is comprised of a crown 11 extending above the gum tissue 12, at least one root portion 13 received within a respective alveolus 14, and a neck portion 16 joining the root and crown at the cemento-enamel junction. The alveoli are deep depressions in the bone tissue of the mandible 17, and are lined with periosteum which is reflected on the tooth at the apex 18 of each root. At the margin of the alveolus the periosteum becomes continuous with the periodontal ligament of the gum tissue 12. The hard tissue of the tooth includes the dentine 21, which provides the primary structure of the tooth, and the very hard enamel layer 22 which forms a durable grinding surface and covers the crown 11 down to the cemento-enamel junction at the neck 16.

Within the dentine layer 21 there is defined a pulp chamber 26. Processes of the pulp chamber 26, termed the root canal 27, are disposed centrally in each root 13 and extend through the respective apex 18 at a minute orifice, the apical foramen 28. The chamber 26 and canal(s) 27 contain dental pulp, a soft, vascular tissue containing numerous nerves and blood vessels and other tissue components. The pulp provides enervation and sustenance to the tooth through the epithelial lining of the pulp chamber and canals.

Figure 2:
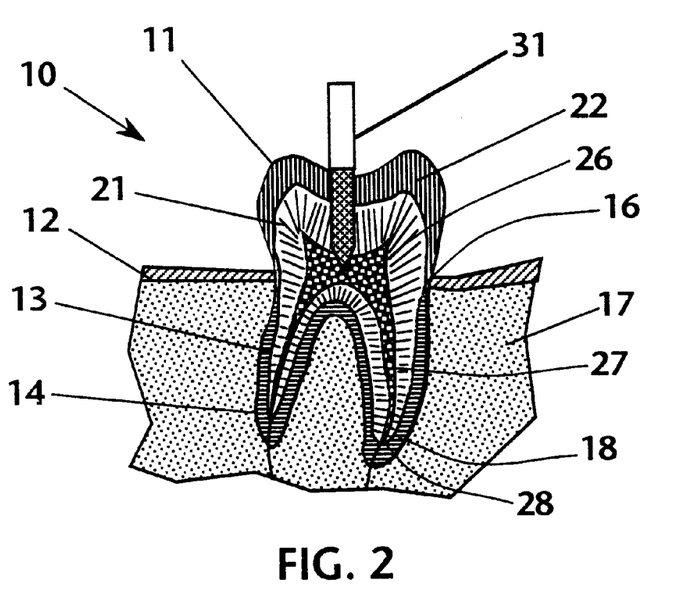
FIG. 2 is a cross-sectional elevation as in FIG. 1, showing the step of creating an opening through the top of the tooth to the pulp chamber within.
Figure 3:
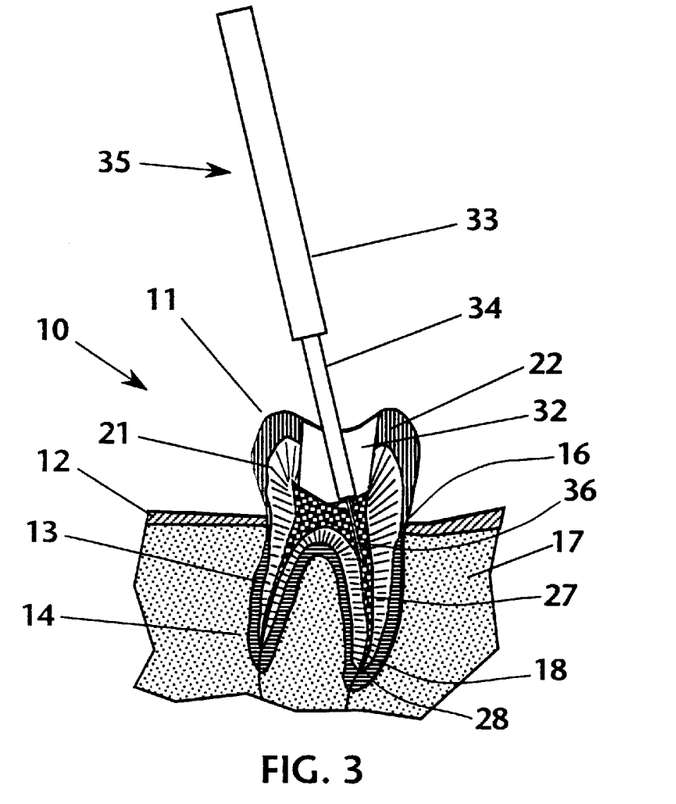
FIG. 3 is a cross-sectional elevation as in FIGS. 1 and 2, showing the cannula of the dental hydrojet tool being extended through the upper opening of the tooth and being actuated to emit a high pressure, high velocity jet.
Figure 4:
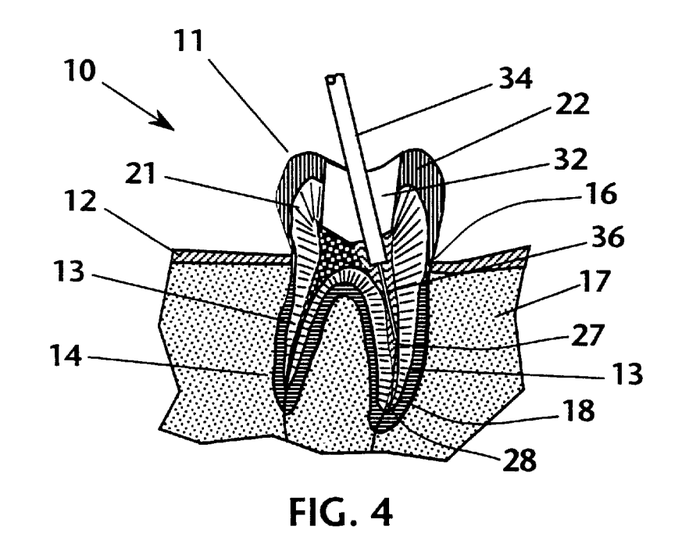
FIG. 4 is a cross-sectional elevation as in FIGS. 1–3, showing the soft tissue within one root channel and a portion of the pulp chamber emulsified and undergoing aspiration.

The method of the present invention is used to treat a tooth that is diagnosed as diseased and requiring a pulpectomy/root canal procedure. With regard to FIG. 2, the tooth is initially opened by employing a dental drill 31 or equivalent burr or grinding tool. The resulting opening 32 extends through the enamel and dentine to provide access to the pulp chamber 26 and root channels 27, as shown in FIG. 3. A dental hydrojet tool 35 is provided, including a handpiece 33 having a cannula 34 extending therefrom. The cannula includes a distal orifice adapted to generate a high velocity, high pressure, low volume jet 36 of liquid. The handpiece maneuvered to insert the cannula 34 into the opening 32 to direct the jet 36 at the soft tissue within the chamber 26 and channels 27. The jet easily cuts through the soft tissue, and the energy and turbulence engendered by the jet causes the tissue to be emulsified upon contact. Moreover, the turbulent liquid easily penetrates into the narrow spaces of the root channels 27 (FIG. 4), effecting thorough excision and emulsification of the nerve and vascular tissue therein. The cannula 34 may also provide vacuum aspiration to remove the emulsified tissue and jet fluid, or a second aspiration cannula may be employed.

In the preferred embodiment the pressure range of the high pressure jet is approximately 500–60,000 psi, and the jet diameter is approximately 10–800 microns. These parameters are selected to provide a liquid jet that is not capable of cutting nor detrimentally eroding the hard tissue of the tooth. As a result, the excision and emulsification action of the jet 36 cannot pass through the apical foramen 28 of the root, if the foramen is naturally closed, and thus cannot injure the alveolar sac or periosteum at the base of the root. Thus a source of substantial post-operative complications in prior art procedures is completely eliminated by the self-limiting feature of the invention.

Figure 5:
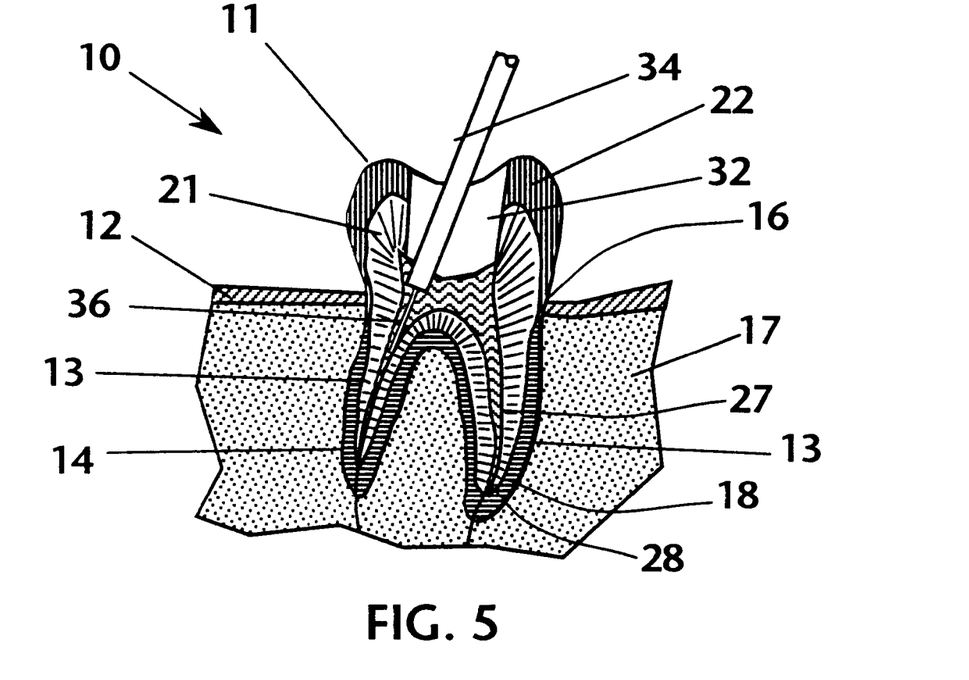
FIG. 5 is a cross-sectional elevation as in FIGS. 1–4, showing the soft tissue within both root channels and all the pulp chamber emulsified and undergoing aspiration.

The jet 36 acts quickly within the soft tissue, and the time necessary to excise, emulsify, and aspirate all the soft tissue within a typical tooth is approximately 10–240 seconds. Of course, more time is required for teeth such as molars having a plurality of root channels 27. As shown in FIG. 5, the dental hydrojet tool 35 may be maneuvered to direct the cannula 34 and jet 36 into each of the root channels to remove all soft tissue therein.

The liquid which constitutes the jet 36 may comprise sterile water or medical grade saline solution, or an antiseptic solution, or an antibiotic solution, or an abrasive solution, or other medications or chemicals, or any combination thereof. Furthermore, more than one of these types of solutions may be used in serial order. For example, saline solution may be used for the excision and emulsification process, followed by an abrasive solution to scour the cavity, an antiseptic solution to eliminate indigenous bacteria and then an antibiotic solution to prevent regrowth of infective agents. It should be noted that the fluid jet may comprise a pulsed jet formed by a pulse intensifier device in the handpiece of the dental hydrojet tool, as described in the US patent to Bair referenced above. Alternatively, the handpiece may be connected to a source of high pressure fluid to form a steady stream jet emanating from the orifice.

Figure 6:
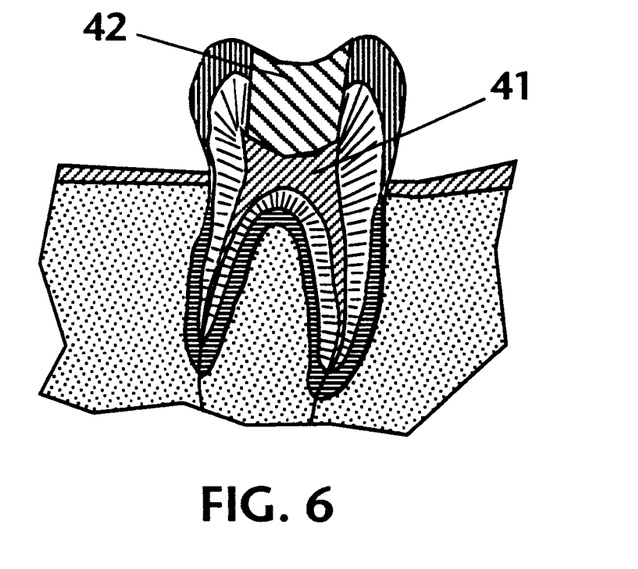
FIG. 6 is a cross-sectional elevation as in FIGS. 1–5, showing the pulp chamber and root channels packed with filler material and the upper opening filled at the completion of the procedure.

After the pulp chamber and root channels have been fully aspirated and visualized for verification of removal, the pulp chamber and root channels are packed with an inert, aseptic material 41, as is known in the dental art. Thereafter, the opening 32 is filled using a standard dental material 42, such as silver amalgam, gold inlay or crown, cured composite material, or the like. The procedure is thus completed.

The use of the dental hydrojet to perform the pulpectomy/root canal procedure exhibits the following advantages over prior art techniques:

1) Complete removal of all soft tissue within the pulp chamber and root channels;
2) Rapid completion, resulting in reduced use of anesthetic and reduced pain experienced by patient, and reduced cost of skilled dentist and office overhead expenses;
3) Elimination of complications due to perforation of root or apical foramen;
4) Sterilization of operating field by use of appropriate jet liquids to minimize post-operative infection.

Figure 7:
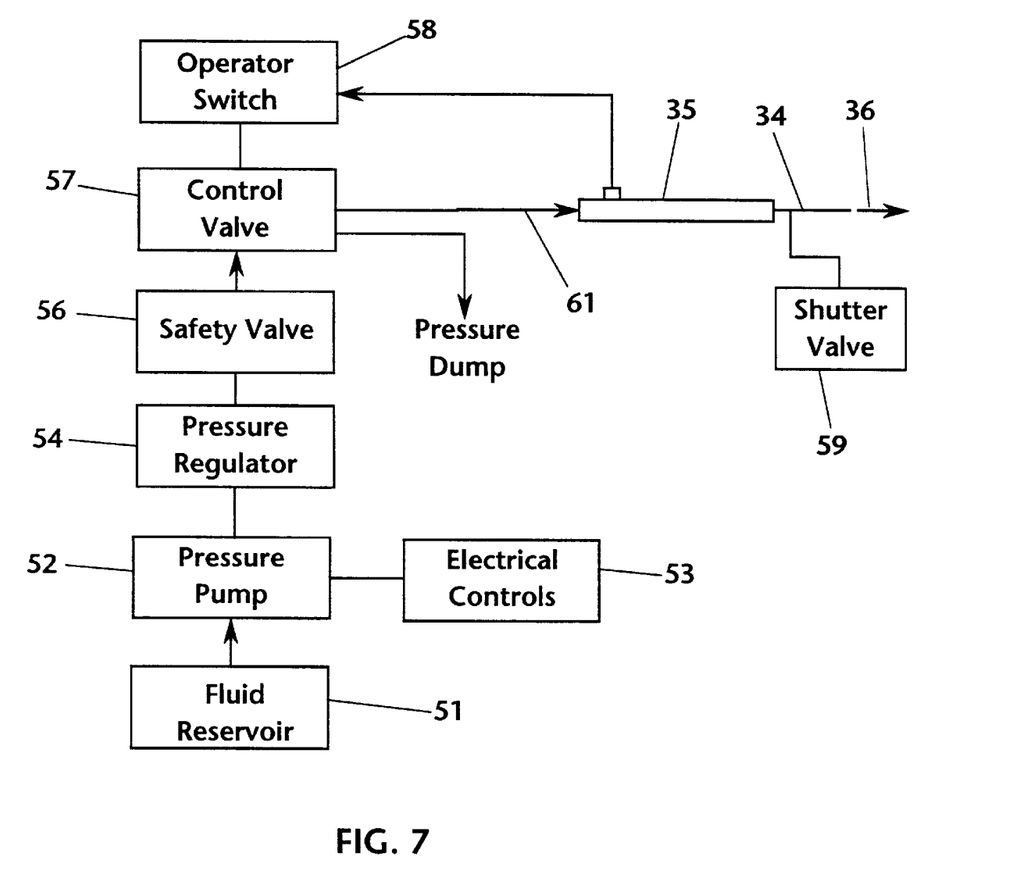
FIG. 7 is a functional block diagram of an electrically driven system for operating the high pressure jet dental instrument of the present invention.

With regard to FIG. 7, an apparatus for carryout out the procedure described above includes a fluid reservoir 51 for supplying the working fluid to the dental hydrojet instrument 35. The fluid from reservoir 51 is fed to a pressure pump 52 to raise the fluid pressure to the range indicated above. The pump 52 is controlled by electrical controls 53 set by the system operator or dentist. A pressure regulator 54 limits the output pressure of the pump 52, and a safety valve 56 provides a pressure cutout function if a set of safety conditions are not present. The pressurized fluid is fed from the safety valve 56 to a control valve 57. The pressurized fluid output from the control valve 57 is fed selectively via a flexible tubing 61 to the dental hydrojet tool 35, which emits the high pressure jet 36 under the direction of the dentist or other trained practitioner.

Output of the control valve 57 is provided on demand of the user by a switch 58, such as a footswitch or an on-off switch on the tool 35. The control valve has the further function of a pressure dump to immediately relieve pressure in the line 61 whenever the switch 58 is turned off, whereby the high pressure jet 36 is squelched instantaneously. In situations where a more immediate and precise cutoff of the jet 36 is required, a shutter valve 59 may be provided at the output end of the hydrojet tool 35 to mechanically block the jet output.

Figure 8:
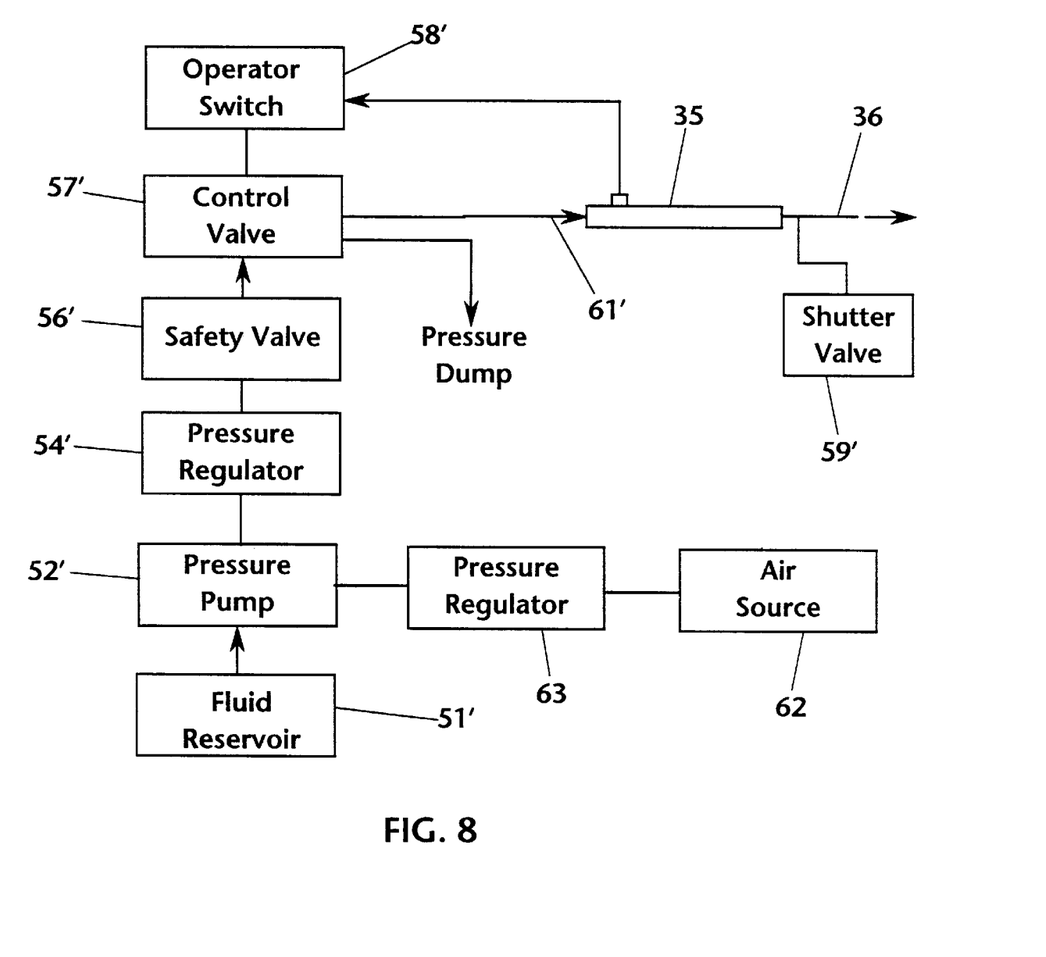
FIG. 8 is a functional block diagram of a pneumatically driven system for operating the high pressure jet dental instrument of the present invention.

With regard to FIG. 8, an apparatus for carrying out dental procedures is depicted which is similar to the apparatus of FIG. 7, and common elements or components are provided with the same reference numerals having a prime (') designation. The primary distinction of the apparatus of FIG. 8 is the provision of an pressurized air source 62, which feeds pneumatic pressure through a pressure regulator 63 to drive a pneumatically operated pressure pump 52'. The remaining components operate substantially as described with reference to FIG. 7.

Either of the apparatus described in FIGS. 7 or 8 may be housed in a small cabinet adapted in size and shape to be placed in a dental office or medical office.

Figure 9:
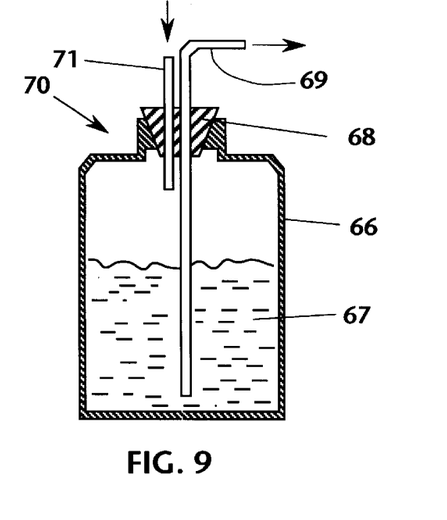
FIG. 9 is a cross-sectional elevation of one embodiment of the fluid reservoir depicted in FIGS. 7 and 8.

With regard to FIG. 9, one embodiment 70 of the fluid reservoir 51 or 51' includes a tank 66 having a charge of fluid 67 retained therein. A stopper 68 seals the tank opening, and a delivery tube 69 extends through the stopper to the bottom of the tank 66. Another tube 71 extends through the stopper to pressurize the head space in the tank and cause the fluid 67 to flow through the delivery tube 69 to the pressure pump 52 or 52'.

Figure 10:
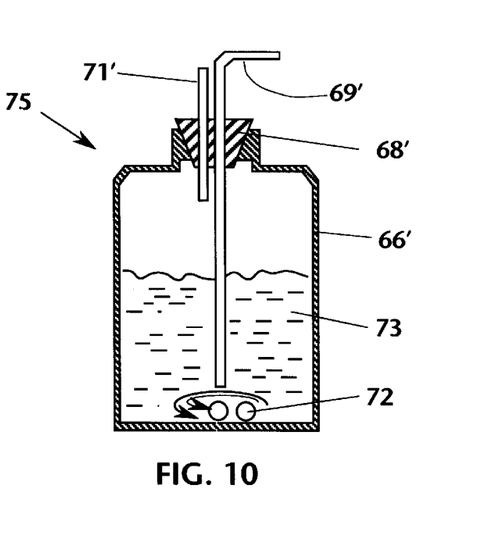
FIG. 10 is a cross-sectional elevation of another embodiment of the fluid reservoir depicted in FIGS. 7 and 8.

A further embodiment 75 of the fluid reservoir, shown in FIG. 10, includes some components similar in function to those of FIG. 9, and are provided with the same reference numerals with a prime(') designation. The tank 75 holds a charge of abrasive solution 73 for use in those procedures which benefit from an abrasive fluid jet. The abrasive solution is stirred by a mechanical stirrer device, as in known in the prior art, and may comprise agitating balls 72 which are magnetically driven by an external magnetic device, or may comprise agitating paddles, or may comprise a device for rocking or oscillating the tank 75 to maintain the abrasive compound suspended in the fluid.

Figures 11, 12:
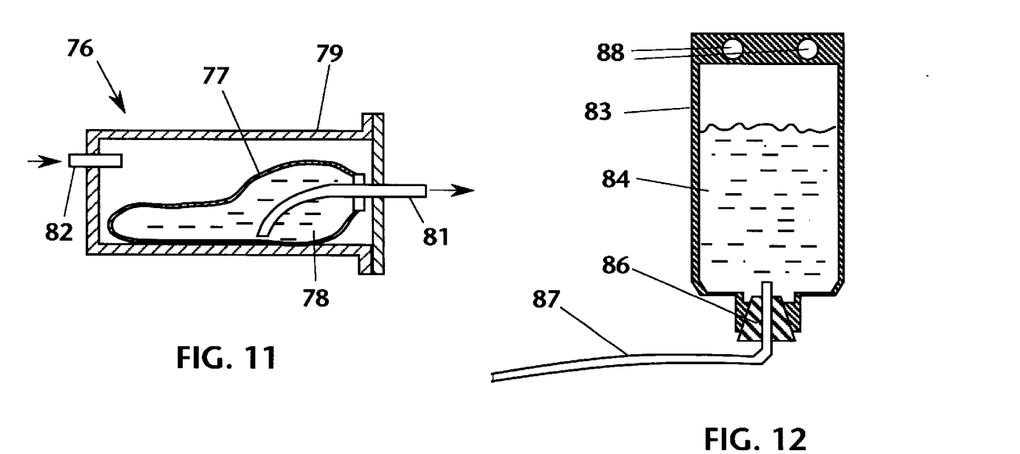
FIG. 11 is a cross-sectional elevation of a further embodiment of the fluid reservoir depicted in FIGS. 7 and 8.
FIG. 12 is a cross-sectional elevation of one more embodiment of the fluid reservoir depicted in FIGS. 7 and 8.

With regard to FIG. 11, another embodiment 76 of the fluid reservoir of the invention includes a sealed bag 77 of premixed fluid 78 for use by the hydrojet instrument. The bag 77 is placed in a sealable vessel or pressure transfer tank 79, and a discharge port 81 extends from within the bag 77 through the vessel to connect to the pressure pump 52. The vessel 79 includes a port 82 connected to a pressurized fluid source, such as the output of the safety valve 56 or 56', whereby the pressure within the vessel causes the premixed fluid 78 to flow from the discharge port 81 at the regulated pressure of the pump 52. In this arrangement the fluid in reservoir 51 or 51' need not be sterile, as the sealed bag 77 prevents contamination of the premixed fluid 78.

A simplified source of hydrojet fluid, shown in FIG. 12, comprises a bag 83 of premixed jet fluid 84. The bag includes a seal 86 at one end, through which a drain tube 87 extends to connect the fluid 84 to the pump 52. The bag further includes means such as holes 88 at the other end of the bag to facilitate hanging the bag in inverted fashion, as shown, similar to an IV bag, whereby the fluid will drain gravitally from the bag 83.

Figure 13:
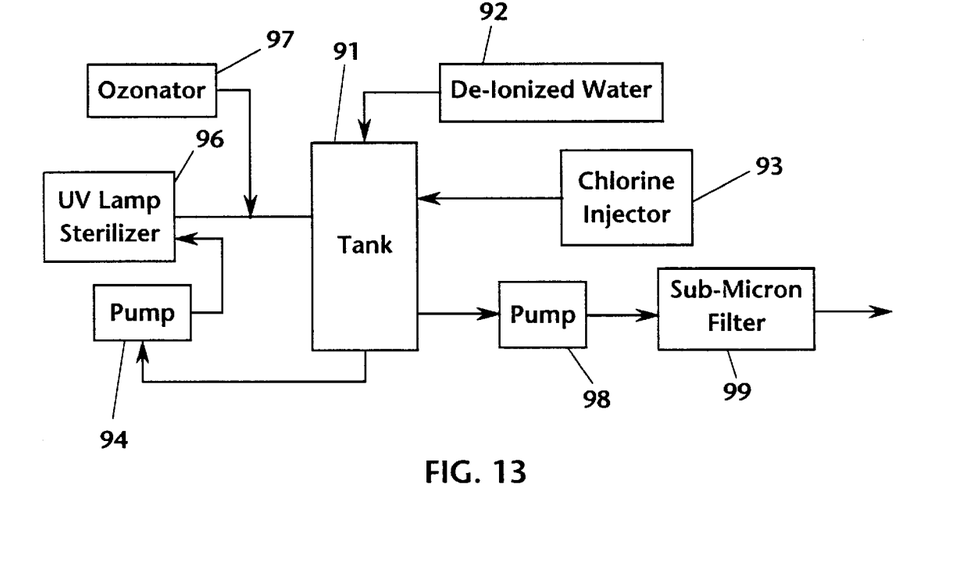
FIG. 13 is a functional block diagram of a system for generating purified water for use in the fluid reservoir of the invention.

A further aspect of the invention is the provision of a system for producing the sterile fluid used in the dental hydrojet tool 35. With regard to FIG. 13, a tank 91 is filled and replenished by a source 92 of de-ionized water. A chlorine injector 93 adds chlorine gas or a chlorine compound to the tank to provide primary water purification. In addition, a pump 94 draws water from the tank and delivers it to an ultraviolet light sterilizer 96. As the water passes from the sterilizer 96 back to the tank 91, an ozonator 97 adds ozone to the water to further sterilize the liquid. The combination of chlorine, UV light, and ozone is effective in eliminating bacterial, viral, and parasitic organisms from the water, thereby reducing to an absolute minimum the opportunity for infection from use of the dental hydrojet tool. The sterile fluid is drawn from the tank 91 by a pump 98 and passed through a sub-micron filter 99, and thence fed either directly to the reservoir 52 or 52', or to any of the reservoir embodiments disclosed herein.

Figure 14:
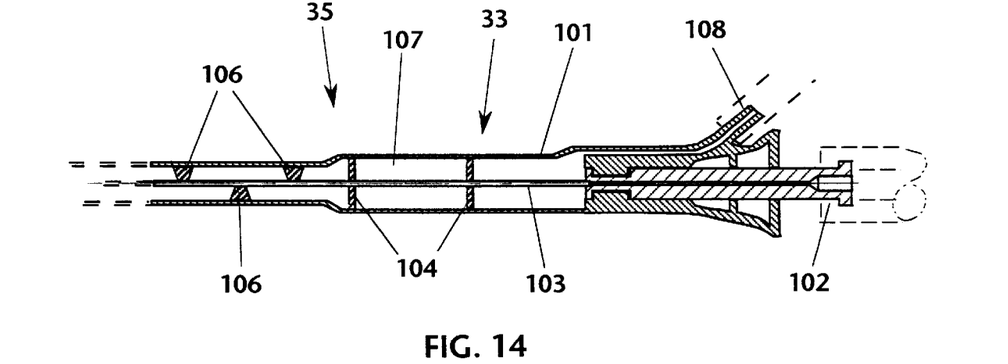
FIG. 14 is a cross-sectional side view of the handpiece portion of the high pressure jet dental instrument of the present invention.

With reference to FIG. 14, the handpiece 33 of the dental hydrojet instrument 35 includes a tubular barrel 101, and a tubing connector 102 joined concentrically to a proximal end of the barrel 101. A jet tube 103 extends distally and concentrically from the connector 102, and is maintained centered in the barrel by a plurality of spider spacers 104 and spacing lugs 106. The connector 102 is adapted to be joined to the tubing 61 that supplies high pressure fluid, and the jet tube 103 extends to the distal end of the cannula 34. The interior space 107 of the barrel 101 comprises an evacuation channel for fluid and debris, and is joined through connector 108 to a vacuum aspiration system.

Figures 15A, 15B:
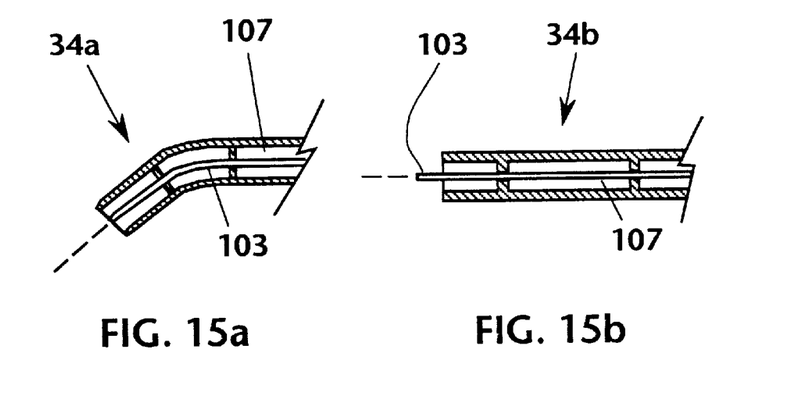
FIG. 15a–15d are cross-sectional side views of different embodiments of output tips of the dental instrument depicted in FIG. 14.
Figure 15C:
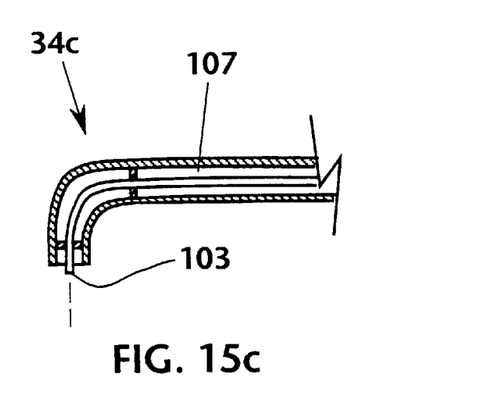
Figure 15D:
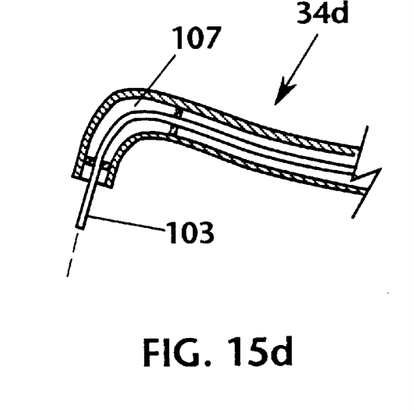

The distal end of the cannula 34 extending from the handpiece 35 may be provided with various angular conformations, as shown in FIGS. 15a–15d. With reference to FIG. 15a, the tip 34a may be angled at approximately 0°–60° from the axis of the instrument, with the distal end of the jet tube 103 generally flush with the distal opening of the cannula. The open end of the cannula provides aspiration and removal of the fluid and debris through channel 107 and connector 108. As shown in FIG. 15b, the cannula tip 34b may extend linearly with the axis of the instrument, with the jet tube 103 extending distally of the end of the tip of the cannula. The extended jet tube provides enhanced visualization of the hydrojet and its impingement on the target. Moreover, in the root canal procedure described above the extended jet tube may be inserted into the pulp chamber and root canals, thereby facilitating completion of the procedure. FIGS. 15c and 15d depict cannula tips 34c and 34d, each including an angular bend of 60°–120° to extend into an opened tooth and to reach other more obscure targets within the mouth. In addition the tip 34d is provided with a curved portion adjacent to the tip.

Figures 16A, 16B:
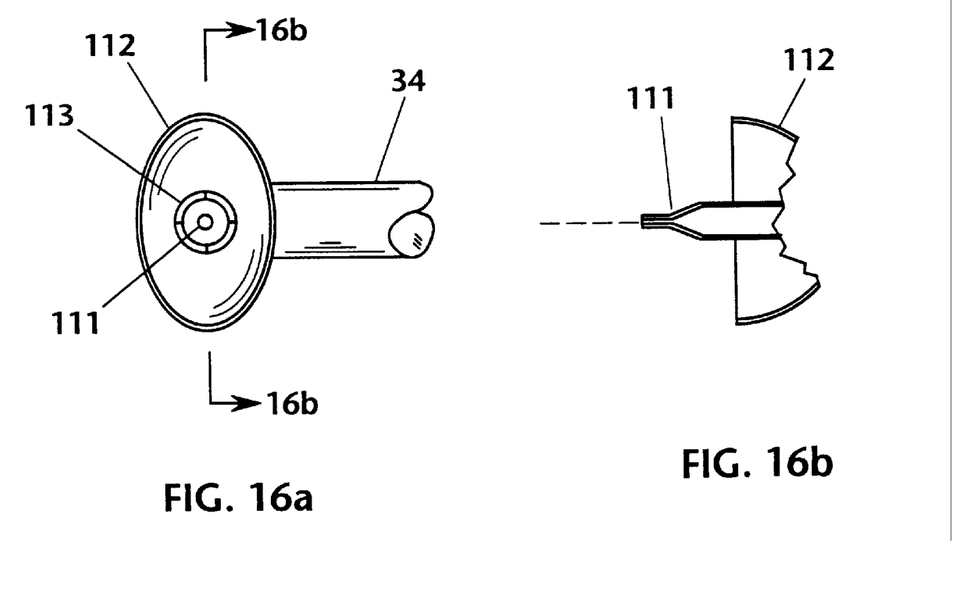

With regard to FIGS. 16a and 16b, a further embodiment of the distal end of the cannula 34 includes a jet-forming nozzle 111 extending at a right angle to the cannula 34 and coupled to the jet tube 103. Extending about the nozzle 111 is a bell-shaped shield 112 having a curved conformation such as any conic section curve and formed preferably of transparent plastic or the like. A gap 113 between the shield 112 and the jet nozzle 111 provides an aspiration intake port, and is connected to the aspiration channel 107 of the cannula. The shield captures a large amount of the spray created by the hydrojet impact on a target, while the transparent plastic permits visualization of the target.

It may be appreciated that the dental hydrojet instrument disclosed herein may be employed to carry out other treatments and procedures in addition to root canal and pulpectomy. For example, the fluid jet is exceptionally well suited to carry out removal of calculus and plaque, and for root planing. This process may be enhanced through the use of an abrasive solution as the fluid for the fluid jet. Likewise, the fluid jet may be used for excision and resection of the gingiva, removal of granulated tissue, as well as mucoosseous surgery. The fluid jet may also be an adjunct to tooth extraction, in that the jet may be used to sever the fibrous attachments to the tooth root, thereby easing the subsequent extraction. These procedures may be aided by the use of antibiotic solutions to form the fluid jet.

Furthermore, a fluid jet of sufficient energy may be used to remove carious dental tissue, thereby providing simple caries removal and preparation for filling. It has been found that proper choice of jet energy selectively removes the carious tissue while the health surrounding enamel and dentine may remain unscathed by the jet. This process may be enhanced through the use of an abrasive solution as the fluid for the fluid jet.

The dental hydrojet instrument provides all of these treatment options, as well as the root canal/pulpectomy procedure, while creating virtually no heat or vibration at the target site. This characteristic is a notable advance over prior art mechanical tools, ultrasound instruments, and dental lasers.

The foregoing description of the preferred embodiments of the invention has been presented for purposes of illustration and description. It is not intended to be exhaustive or to limit the invention to the precise form disclosed, and many modifications and variations are possible in light of the above teaching without deviating from the spirit and the scope of the invention. The embodiments described are selected to best explain the principles of the invention and its practical application to thereby enable others skilled in the art to best utilize the invention in various embodiments and with various modifications as suited to the particular purpose contemplated. It is intended that the scope of the invention be defined by the claims appended hereto.

What is claimed is:

1. A method for removal of carious tissue from a tooth, including the steps of:

provide a dental hydrojet tool having an orifice adapted to emit a high pressure, high velocity liquid jet;

directing the high pressure, high velocity liquid jet at the carious tissue to erode and excise the carious tissue; and, aspirating and removing the eroded and excised carious tissue, further including the step of selecting a range of velocity and pressure for said liquid jet that provides sufficient kinetic energy to effect erosion and excision of the carious tissue and provides insufficient kinetic energy to substantially affect surrounding healthy dental tissue.

2. The method of claim 1, further including the step of providing a solution containing an abrasive substance to form the liquid of said liquid jet.

3. A method for removal of calculus and plaque tissue from a tooth, including the steps of:

providing a dental hydrojet tool having an orifice adapted to emit a high pressure, high velocity liquid jet;

directing the high pressure, high velocity liquid jet at the calculus and plaque to erode and remove the calculus and plaque, and, aspirating and removing the calculus and plaque, further including the step of selecting a range of velocity and pressure for said liquid jet that provides sufficient kinetic energy to effect erosion of the calculus and plaque and having insufficient kinetic energy to substantially affect surrounding healthy dental tissue.

4. The method of claim 3, further including the step of providing a solution containing an abrasive substance to form the liquid of said liquid jet.

5. A method for surgical removal of soft tissue from the mouth, including the steps of:

providing a dental hydrojet tool having an orifice adapted to emit a high pressure, high velocity liquid jet;

directing the high pressure, high velocity liquid jet at the soft tissue to excise and emulsify the soft tissue, and, aspirating and removing the excised and emulsified soft tissue.

6. The method of claim 5, further including the step of providing a solution containing an antibiotic substance to form the liquid of said liquid jet.

7. The method of claim 5, wherein the soft tissue comprises gingival tissue.

8. The method of claim 5, wherein the soft tissue comprises granulated tissue.

9. The method of claim 5, wherein the soft tissue comprises the indigenous periodontal ligament securing a tooth root in a jaw.

10. A dental hydrojet system, including:

a dental hydrojet instrument having a jet nozzle adapted to emit a high pressure, high velocity liquid jet;

a fluid reservoir for storing a liquid;

pump means connected to said fluid reservoir for pumping said liquid under high pressure to said dental hydrojet instrument;

control means for selectively operating said dental hydrojet instrument to emit said high pressure, high velocity liquid jet, said pump means producing liquid pressure in the range of 4000–30,000 psi; and, said jet nozzle including a jet orifice having a diameter in the range of 20–800 microns.

11. The dental hydrojet system of claim 10, wherein said liquid comprises an antiseptic solution.

12. The dental hydrojet system of claim 10, wherein said liquid comprises an antibiotic solution.

13. The dental hydrojet system of claim 10, wherein said liquid includes an abrasive constituent.

14. The dental hydrojet system of claim 10, wherein said fluid reservoir comprises a sealed bag containing said liquid, and means for conducting said liquid to said pump means.

15. The dental hydrojet system of claim 14, wherein said means for conducting includes a sealed vessel adapted to receive said sealed bag therein, whereby pressure within said sealed vessel pressurizes said liquid and causes it to flow to said handpiece.

16. The dental hydrojet system of claim 10, wherein said control means includes a control valve interposed between said pump means and said dental hydrojet instrument, and means for an operator of said instrument to switch said control valve on and off.

17. A dental hydrojet instrument, including:

a handpiece having a proximal end and a distal end;

a cannula extending from said distal end of said handpiece;

a jet tube extending through said handpiece and said cannula;

means for connecting a proximal end of said jet tube to a source of high pressure liquid;

a jet nozzle at a distal end of said jet tube for emitting a high velocity, high pressure liquid jet, said jet nozzle including a jet orifice having a diameter in the range of 20–800 microns.

18. The dental hydrojet instrument of claim 17, wherein said handpiece includes a tubular barrel extending about a portion of said jet tube.

19. The dental hydrojet instrument of claim 18, further including aspiration means for removing jet fluid and dental tissue.

20. The dental hydrojet instrument of claim 19, said aspiration means including an aspiration channel extending through said handpiece and said cannula.

21. The dental hydrojet instrument of claims 20, wherein said aspiration channel includes the interior of said tubular barrel.

22. The dental hydrojet instrument of claim 21, wherein said aspiration means includes connector means coupled to said interior of said tubular barrel and adapted to be connected to a vacuum aspiration device.

23. A method for removal of all soft tissue within the pulp chamber and root canals of a tooth, including the steps of:

forming an opening through the upper portion of the tooth to gain access to the pulp chamber;

providing a dental hydrojet tool having an orifice adapted to emit a high pressure, high velocity liquid jet;

directing the high pressure, high velocity liquid jet at the soft tissue within the pulp chamber and root canals of the tooth to excise and emulsify the soft tissue;

aspirating and removing the excised and emulsified soft tissue from the pulp chamber and root canals;

filling the pulp chamber and root canals with a dental filling compound; and, closing the opening through the upper portion of the tooth with a dental preparation;

wherein the liquid jet is emitted in a pressure range of 500 psi to 30,000 psi.

24. A method for removal of all soft tissue within the pulp chamber and root canals of a tooth, including the steps of:

forming an opening through the upper portion of the tooth to gain access to the pulp chamber;

providing a dental hydrojet tool having an orifice adapted to emit a high pressure, high velocity liquid jet;

directing the high pressure, high velocity liquid jet at the soft tissue within the pulp chamber and root canals of the tooth to excise and emulsify the soft tissue;

aspirating and removing the excised and emulsified soft tissue from the pulp chamber and root canals;

filling the pulp chamber and root canals with a dental filling compound; and, closing the opening through the upper portion of the tooth with a dental preparation;

wherein the liquid jet has a diameter in the range of 20 microns to 800 microns.

25. A method for removal of all soft tissue within the pulp chamber and root canals of a tooth, including the steps of:

forming an opening through the upper portion of the tooth to gain access to the pulp chamber;

providing a dental hydrojet tool having an orifice adapted to emit a high pressure, high velocity liquid jet;

directing the high pressure, high velocity liquid jet at the soft tissue within the pulp chamber and root canals of the tooth to excise and emulsify the soft tissue;

aspirating and removing the excised and emulsified soft tissue from the pulp chamber and root canals;

filling the pulp chamber and root canals with a dental filling compound; and, closing the opening through the upper portion of the tooth with a dental preparation;

further providing a constant source of high pressure liquid to the dental hydrojet tool to deliver a constant jet stream from the orifice.

26. A dental hydrojet system, including:

a dental hydrojet instrument having a jet nozzle adapted to emit a high pressure, high velocity liquid jet;

a fluid reservoir;

a liquid stored in said fluid reservoir;

pump means connected to said fluid reservoir for pumping said liquid under high pressure to said dental hydrojet instrument;

control means for selectively operating said dental hydrojet instrument to emit said high pressure, high velocity liquid jet;

said liquid including an abrasive constituent;

said reservoir means including a tank containing said abrasive solution, and further including stirring means for maintaining said abrasive constituent in solution.

27. A dental hydrojet system, including:

a dental hydrojet instrument having a jet nozzle adapted to emit a high pressure, high velocity liquid jet;

a fluid reservoir for storing a liquid;

pump means connected to said fluid reservoir for pumping said liquid under high pressure to said dental hydrojet instrument;

control means for selectively operating said dental hydrojet instrument to emit said high pressure, high velocity liquid jet;

said control means including a control valve interposed between said pump means and said dental hydrojet instrument;

means for an operator of said instrument to switch said control valve on and off;

said control valve including means for instantly relieving fluid pressure in said instrument whenever said control valve is switched to said off condition.

28. A method for removal of all soft tissue within the pulp chamber and root canals of a tooth, including the steps of:

forming an opening through the upper portion of the tooth to gain access to the pulp chamber;

providing a dental hydrojet tool having an orifice adapted to emit a high pressure, high velocity liquid jet;

directing the high pressure, high velocity liquid jet at the soft tissue within the pulp chamber and root canals of the tooth to excise and emulsify the soft tissue;

aspirating and removing the excised and emulsified soft tissue from the pulp chamber and root canals;

filling the pulp chamber and root canals with a dental filling compound; and, closing the opening through the upper portion of the tooth with a dental preparation;

wherein the liquid jet has sufficient kinetic energy to excise and emulsify the soft tissue within the tooth but has insufficient kinetic energy to cut or substantially erode the hard tissue of the tooth.

29. A method for removal of all soft tissue within the pulp chamber and root canals of a tooth, including the steps of:

forming an opening through the upper portion of the tooth to gain access to the pulp chamber;

providing a dental hydrojet tool having an orifice adapted to emit a high pressure, high velocity liquid jet;

directing the high pressure, high velocity liquid jet at the soft tissue within the pulp chamber and root canals of the tooth to excise and emulsify the soft tissue;

aspirating and removing the excised and emulsified soft tissue from the pulp chamber and root canals;

filling the pulp chamber and root canals with a dental filling compound; and, closing the opening through the upper portion of the tooth with a dental preparation;

wherein the liquid jet has sufficient kinetic energy to excise and emulsify the soft tissue within the tooth but has insufficient kinetic energy to perforate a closed apical foramen of the root canal.

30. A method for removal of all soft tissue within the pulp chamber and root canals of a tooth, including the steps of:

forming an opening through the upper portion of the tooth to gain access to the pulp chamber;

providing a dental hydrojet tool having an orifice adapted to emit a high pressure, high velocity liquid jet;

directing the high pressure, high velocity liquid jet at the soft tissue within the pulp chamber and root canals of the tooth to excise and emulsify the soft tissue;

aspirating and removing the excised and emulsified soft tissue from the pulp chamber and root canals;

filling the pulp chamber and root canals with a dental filling compound; and, closing the opening through the upper portion of the tooth with a dental preparation;

further providing a pressure intensifier device within the dental hydrojet tool to generate and deliver pulses of high pressure liquid to the orifice.

* * * * *